United States Patent

Gemra

[11] Patent Number: 5,479,830
[45] Date of Patent: Jan. 2, 1996

[54] ANCHORAGE HARDWARE TESTING DEVICE

[75] Inventor: Richard J. Gemra, Millington, N.J.

[73] Assignee: Bell Communications Research Inc., Livingston, N.J.

[21] Appl. No.: 341,724

[22] Filed: Nov. 18, 1994

[51] Int. Cl.[6] .................................................. G01N 3/08
[52] U.S. Cl. ................................................. 73/826; 73/788
[58] Field of Search ........................... 73/81, 788, 803, 73/818, 821, 838, 841, 826, 827, 834, 831, 832

[56] References Cited

U.S. PATENT DOCUMENTS

| | | | |
|---|---|---|---|
| 3,443,423 | 5/1969 | Lou Ma | 73/821 |
| 3,732,725 | 5/1973 | Allen, Jr. et al. | 73/81 |
| 4,036,474 | 6/1977 | Owan | 254/124 |
| 5,394,753 | 3/1995 | Moriyoshi | 73/818 |

*Primary Examiner*—Richard Chilcot
*Assistant Examiner*—Max H. Noori
*Attorney, Agent, or Firm*—Leonard Charles Suchyta; Michael S. Slomin

[57] ABSTRACT

A device for the testing of anchorages in, protrusions from, or attachments to surfaces (collectively, "anchorage hardware") is connected to the anchorage hardware under test and rests against the surface. A slidable coupler is positioned within an enclosure under a mounting plate and to which the hardware to be tested is attached. A spring within part of the device is used to apply a calibrated loading force between the anchorage and the surface. A cam determines the spacing between the enclosure and a spring assembly housing, causing motion of the coupler and transfer of the force of the spring to the hardware under test. The device may include an indicator to measure the force applied.

20 Claims, 4 Drawing Sheets

ANCHORAGE HARDWARE TESTING DEVICE

TECHNICAL FIELD OF THE INVENTION

This invention relates to an anchorage testing device for determining whether an anchorage in, a protrusion from, or an attachment to a surface can withstand a designated load without impairing the attachment to the surface.

BACKGROUND OF THE INVENTION

In many industries and fields of endeavor, attachments are made to surfaces for purposes of mounting, attaching, or joining equipment, assemblies or apparatus to these surfaces. Such attachments might be to structures, to equipments, or to apparatus. Such attachment may be made by welding, adhesive, joining, anchorage devices, threaded lugs, threaded nuts or similar elements.

It is important in some applications to determine whether an attachment can withstand a designated load, and this is often accomplished by applying a static load to the attachment to determine whether it can withstand the load without separating from the surface or otherwise failing. Typically, the load applied during testing exceeds the load to be applied in service.

An example of this might be an attachment of a pipe to a concrete ceiling. The attachment might be made by drilling a hole in the concrete, placing a lead or composition anchor therein, and connecting a pipe or cable hanger to the anchor with a bolt. This attachment system must withstand, at minimum, the weight of the hanger and bolt and the weight of the pipe. A test of its ability to do so would apply a force equivalent to the force associated with that weight, plus a safety factor.

One way that this has been done in the past has been to attach varying calibrated weights to the attachment system. However, this is fully effective only if the attachment is vertical, i.e. to a ceiling, and the normal loading force is due to gravity. Furthermore, weights sufficient to apply the thousands of pounds of force that are often needed for structural applications of such testing are bulky, heavy, and difficult to carry and maneuver and could create safety problems. In a crowded environment, equipment or assemblies may have to be moved or detached to provide space for bulky weights or test apparatus.

Another way that this has been done in the past has been to utilize pneumatic or hydraulic apparatus to generate the loading. However, this requires compression or pumping apparatus which is bulky and not readily portable and maintenance of seals for the equipment to continue to operate reliably. Furthermore, a large area around the particular attachment under test has had to be cleared during testing using pneumatic devices and may similarly have had to be cleared if weights are used. This has been a problem in the telephone industry, where ceiling and wall anchors are used to attach a variety of cable racks, tracks, or ducts in facilities such as central offices and cable vaults. Because space is often at a premium in these locations, to perform testing of added attachments using pneumatic devices or weights it has been necessary to move existing cables, which can impermissibly disrupt services carried on them. This has hindered the ability to perform testing.

In view of these shortcomings, it is an object of the present invention to provide a device that facilitates the application of designated static loads to anchorage hardware to determine its ability to sustain loads. While my invention is herein described to test anchorage hardware used to attach cable racks and pipes to the ceilings, walls and floors of structures, it is not so limited in its application. The invention may also be used to test protrusions or attachments to surfaces of equipments or apparatus. Further use of the term anchorage, herein, includes other such elements as attachments, protrusions and extensions.

SUMMARY OF THE INVENTION

These and other objects are attained in accordance with embodiments of my invention wherein the anchor or equipment to be tested is attached to one end of a rod, the other end of which is attached a slidable coupler. A spring within a spring assembly housing is also connected, as by a rod or plunger, to the slidable coupler. In accordance with an aspect of my invention, a cam is positioned between wear or bearing plates on the surface of the spring housing and the facing surface of the enclosure attached to the bottom of the mounting plate and within which the slidable coupler is positioned. Rotation of the cam increases the spacing between the spring housing and the enclosure, thereby changing the force applied by a calibrated spring within the housing and applying the test loading force to the apparatus being tested. A gauge attaching to the lower end of the spring to the spring housing indicates the load being applied.

My test device can be used in many applications. One specific application is to evaluate the integrity of field installed concrete anchors used in the telephone plant for securing equipment, cable racks, etc. My inventive test device applies a load, as noted by the gauge, to anchorage hardware in ceilings, floors and walls of telephone buildings, in this specific example, to determine their ability to sustain loads By utilizing different springs maximum different loads can be specified. Alternatively, as described later, an extension or a leverage bar may be used to scale the load.

Load testing devices in accordance with my invention are position independent and thus can be used on anchors attached to ceilings, floors and walls, or oblique surfaces or on other equipments. The load testing device is small, light, and highly portable and can be used in confined spaces without detachment or rearrangement of equipments or other apparatus.

DETAILED DESCRIPTION

Figure 1:
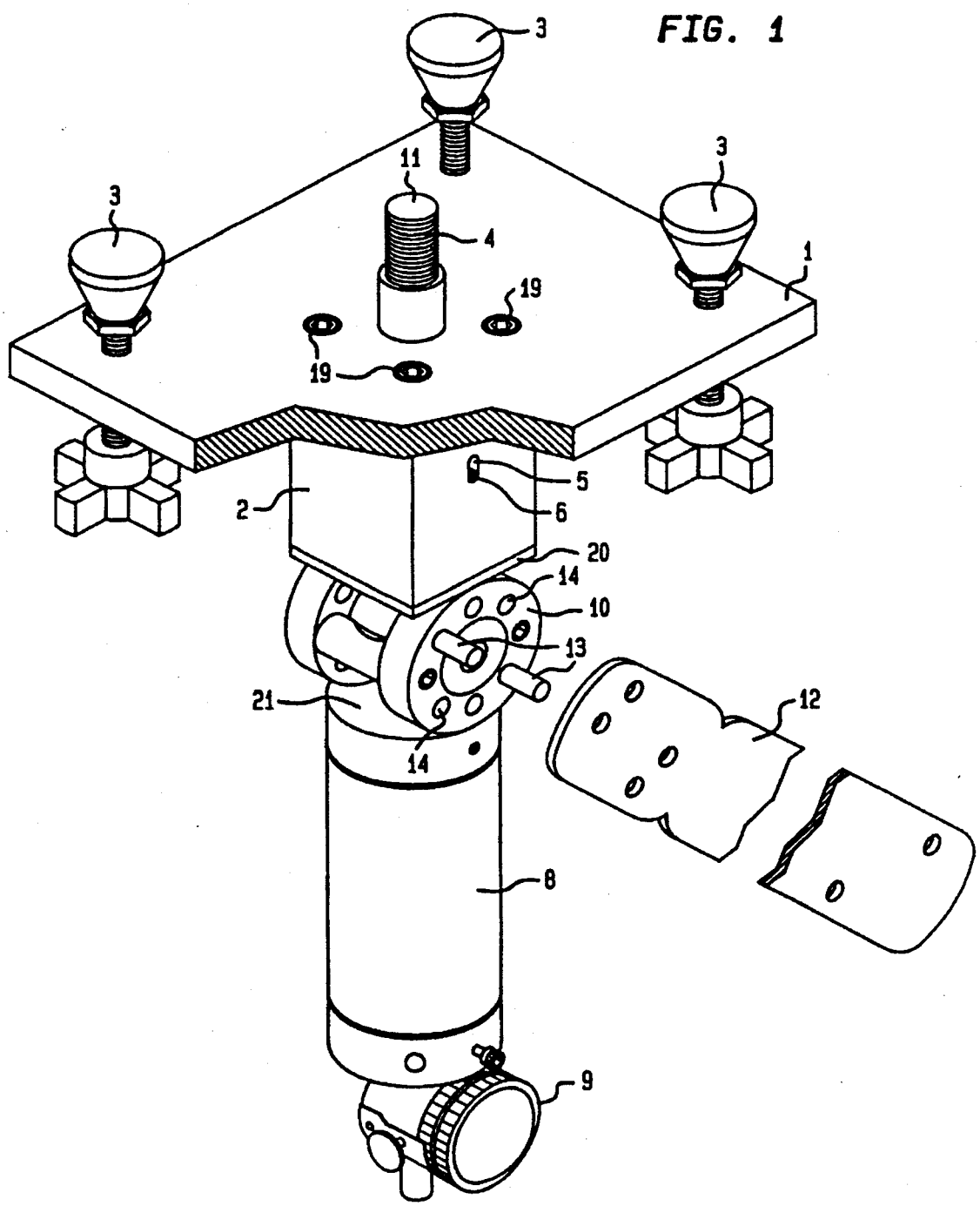
FIG. 1 is a perspective view of an anchorage hardware testing device in accordance with my illustrative embodiment of my invention.

FIG. 1 depicts an illustrative embodiment of the anchorage hardware testing device of my invention. In this embodiment, the device consists of a metallic frame or plate 1 to which is attached an enclosure 2 as by rivets 19, and on which are multiple leveling pads or jack screws 3; in FIG. 1 the plate or frame 1 is shown partially broken away to allow the other elements of my invention to be seen in perspective. Advantageously four leveling pads 3 are utilized. A threaded rod 4 passes through a hole in the frame and hence into the enclosure.

Figure 2:
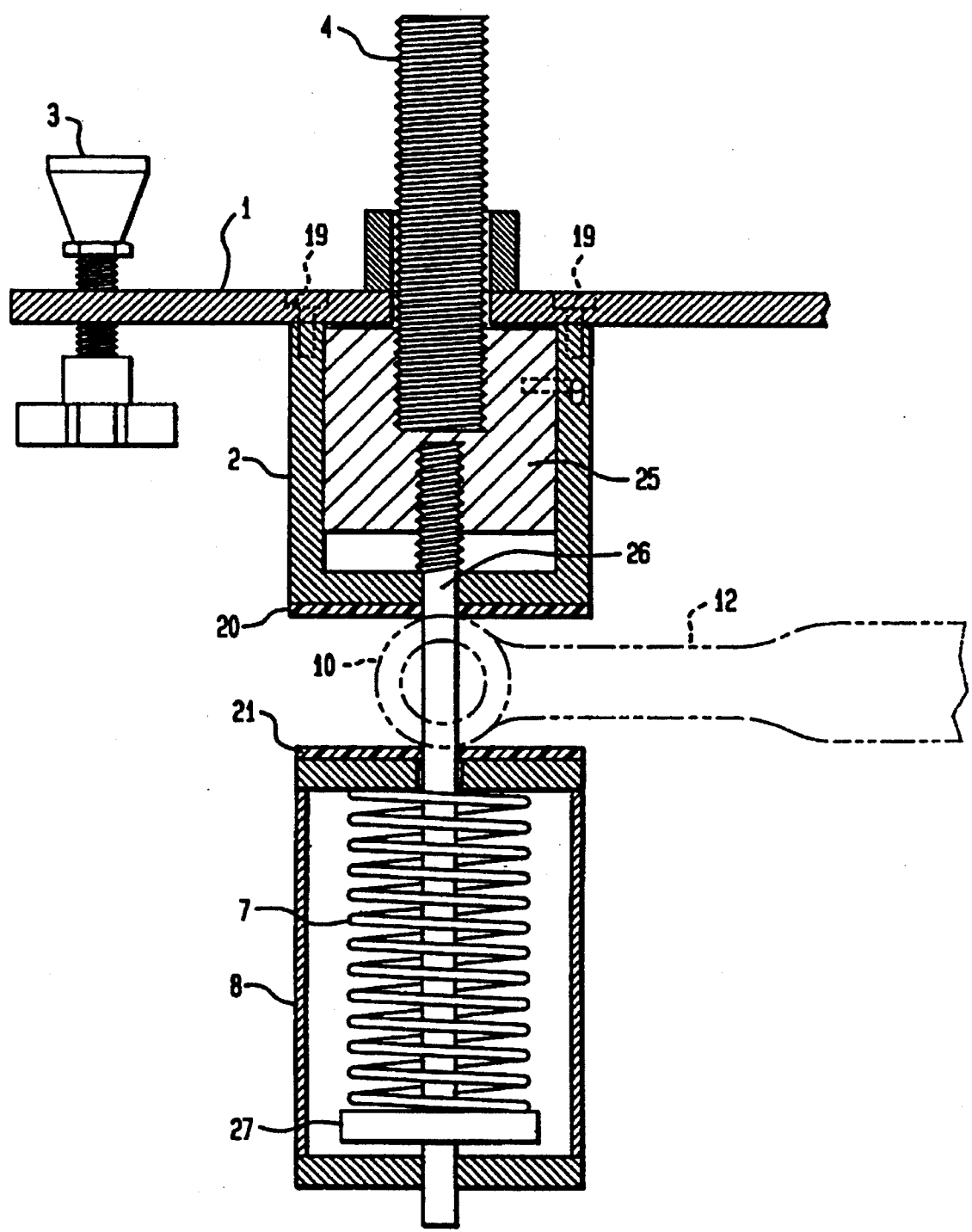
FIG. 2 is a cross sectional view showing the connection of the spring assembly to the slidable coupler within the enclosure secured to the mounting plate, in the embodiment of FIG. 1.

As best seen in FIG. 2, positioned within the enclosure 2 is a slidable coupler 25 into which one end of the rod 4 is screwed. Also threadably connected to the slidable coupler 25 is the end of a rod or plunger 26 extending from a cylindrical spring housing 8. Within the housing 8 is a compression spring 7, though in other embodiments other types of springs or spring washers can be employed. A dial indicator 9 is attached to the end of the cylindrical housing, as seen in FIG. 1 but not depicted in FIG. 2, and measures the displacement of the rod or plunger 26 relative to the flange 27. Advantageously, the coupler 25 is tightly fitted into the enclosure 2.

In accordance with an aspect of my invention, the spring 7 within the spring assembly or housing member 8 generates the calibrated force for the testing of loads through the incremental separation of the spring assembly 8 from the enclosure 2 and specifically in this embodiment through the action of a pair of rotatable cams 10, hereinafter referred to as the cam 10. The cam 10, which may be of an oval or other tapered shape to be longer in the longitudinal direction of the spring housing member 8 as it rotates, is positioned between two wear plates 20 and 21. Wear plate 20 is on the end of the enclosure 2 facing the spring assembly 8 while wear plate 21 is on the top of the housing member 8 facing the enclosure 2. Accordingly, an operator using this embodiment of my invention will rotate the cam 10 to cause a further separation of the housing member 8 from the enclosure 2, thereby compressing the spring 7 within the housing member. Such rotation of the cam 10 thus controls the force of the spring 7 that is transmitted through the coupler 25 and the screw rod 4. The upper end 11 of the screw rod 4 is connected, by appropriate means known in the art and not herein depicted, to the attachment or other body under test. The testing load or force is applied to the anchorage hardware under test by means of the connection at the end 11 of the rod 4 and the upper surface of the plate or frame 1 through the leveling pads 3.

In structural applications, the anchorage hardware to be tested typically includes a threaded lug over which a hanger or bracket may be placed and connected using an appropriate nut or may include a threaded anchor or cylinder into which an appropriate threaded bolt may be screwed. Advantageously, the testing apparatus of my invention may readily be connected to either of these using an appropriate threaded coupler or rod or interposed adapters. Clamping devices or other elements for temporary attachment of the testing device to the attachment being tested may also be employed, as are known in the art, depending on the nature of equipment being tested, whether a concrete anchor in a ceiling or other types of equipment or apparatus. Specifically, in those instances where the anchor being tested itself has a threaded element protruding therefrom, a bridge adapter can be placed between that threaded member and the threaded or screw rod 4 of my invention so that the test device can be applied to the anchor without the need to remove any of the hardware that is in the field and associated with the anchor being tested.

I have also found it advantageous to allow for visual inspection of when the appropriate or designated load has been achieved. This may be readily attained by an aperture 5 extending laterally from the side of the enclosure 2 to the open area within the enclosure 2 wherein the coupler 25 is situated. Specifically, the visual inspection will show the displacement of the coupler 25 within the enclosure 2 and can be used as a pass/fail measure in lieu of the gauge or in addition to the gauge 9. A locator pin 6 may be inserted within the aperture 5 and markings may be placed on the adjacent side of the coupler 25 to facilitate the visual identification of when movement of coupler 25 relative to enclosure 2 occurs.

I have found that large increases in load can be attained with very slight tapering of the surface of the cam 10. Specifically, forces of 1200 pounds, as measured by the gauge 9, can be achieved with a taper change in the cam 10 of 0.1 of an inch.

Mechanical advantage in compressing the spring 7 is gained by temporarily connecting a lever handle 12 to the cam 10 using pins 13 that may be placed in appropriate holes 14 in the cam 10 to facilitate such tensioning.

Figure 3:
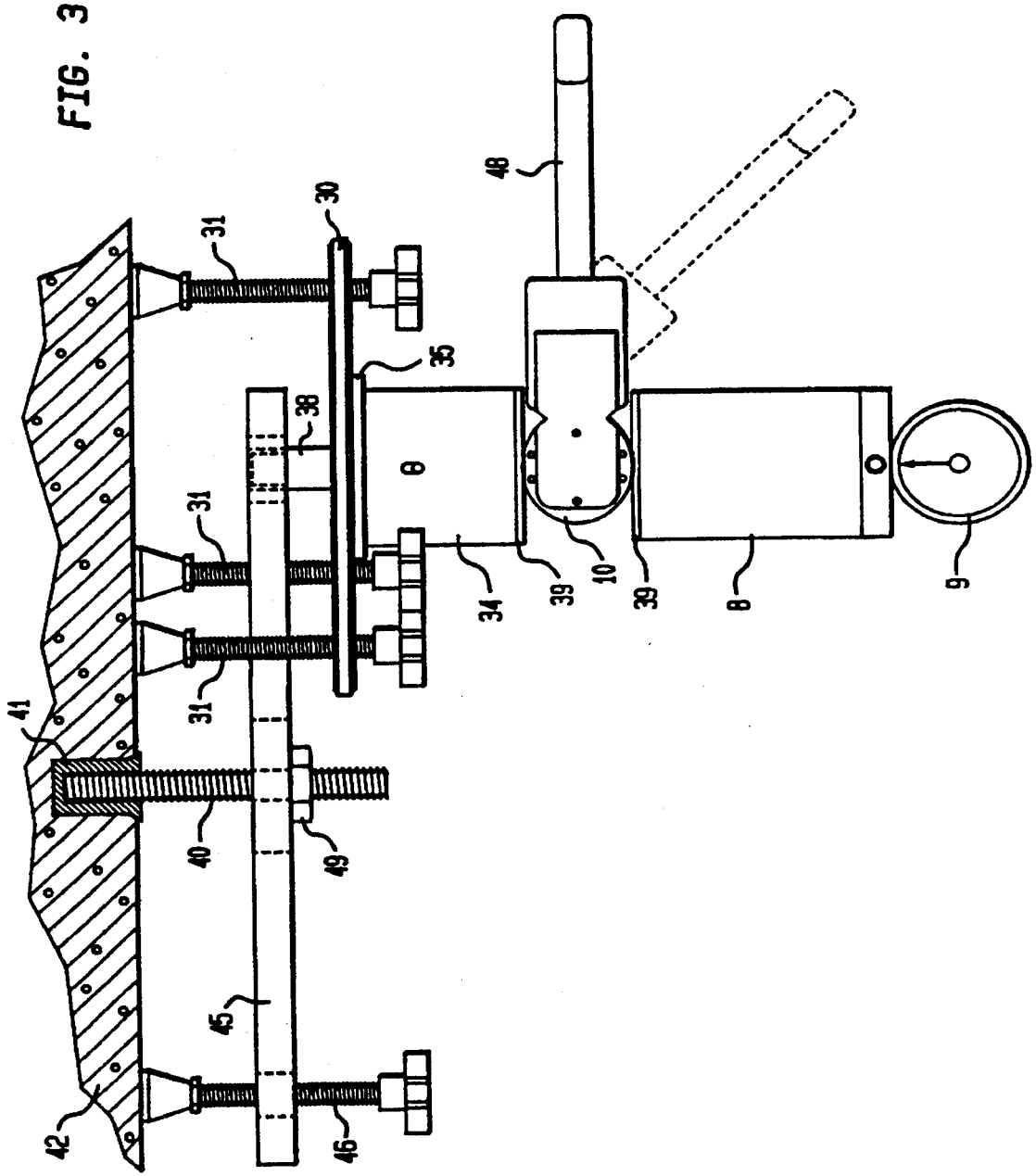
FIG. 3 is a perspective view of a second illustrative embodiment of my invention and depicting its use when the anchorage to be tested is off-set from my device.
Figure 4:
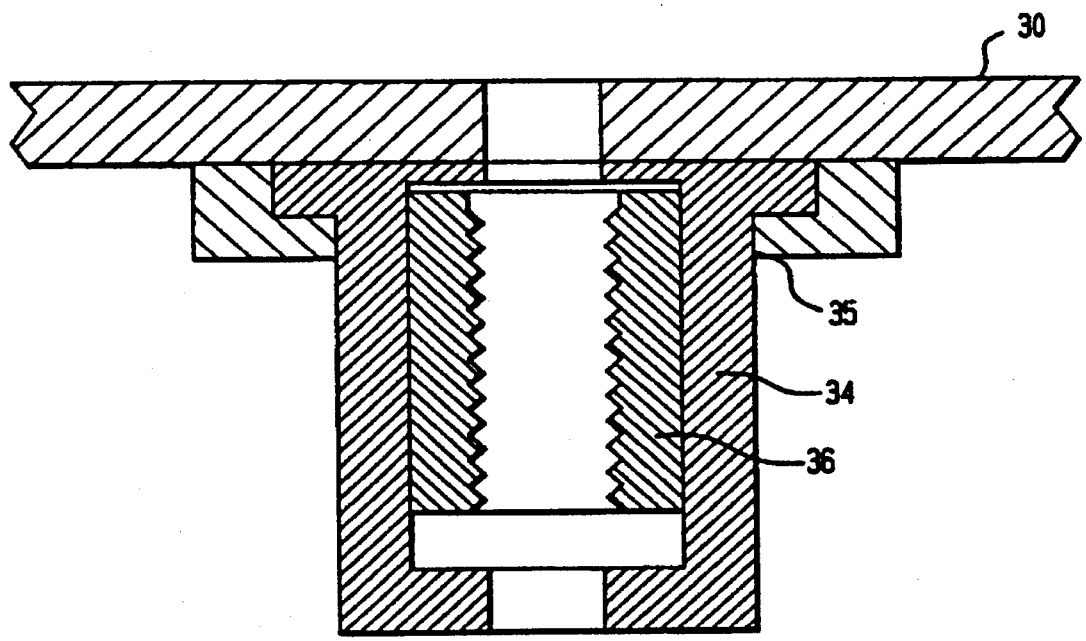
FIG. 4 is a cross-sectional view of the rotatable cylindrical collar or housing and the slidable coupler therein, in accordance with the embodiment of FIG. 3.

FIG. 3 is a perspective view of a second illustrative embodiment of my invention. In this embodiment a circular mounting plate 30 has three leveling pads or jack screws 31. A cylindrical enclosure 34 is rotatably held by a mounting ring 35 at the surface of the plate 30 away from the anchor being tested. Slidably positioned within the cylindrical enclosure 34, as best seen in FIG. 4, is the cylindrical coupler 36 to which, at one end, the rod 38, comparable to the rod 4 in the prior embodiment of FIG. 1, is threadably secured. The spring housing assembly 8 in this embodiment is the same as that of the prior embodiment and the outer end of the plunger on rod 26 is also threadably secured into the cylindrical coupler 36.

As in the prior embodiment, bearing or wear plates 39 are provided on the opposing faces of the cylindrical enclosure 34 and the spring assembly 8, and the cam 10 is interposed between these bearing plates. A crank handle 48 rotates the cam 10 similar to the lever or handle 11 of the prior embodiment. However, a wedge or other gradually varying separating means can be employed in place of the cam 10, within the spirit and scope of my invention, to transfer the force of the calibrated spring 7 to the device under test.

In accordance with another aspect of my invention, as depicted with the embodiment of FIG. 3, my device can be employed in situations where the device cannot be positioned so as to linearly connect the rod 38 to the threaded rod 40 inserted in the anchor 41, as in a concrete ceiling 42. This may be due to intervening equipments or other obstructions. In accordance with another aspect of my invention a split extension bar assembly 45 can be utilized. At one end of the extension bar assembly a screw rod block is provided into which the rod 38 from my testing device can be screwed. At the other end of the bar assembly 45 is provided a threaded support into which the leveling pad or screw jack 46 can be inserted. The rod 40 from the anchor 41 is secured to the split extension bar by a split nut 49. The rod 40 may extend considerably below the extension bar 45 and in situations where my device is being used to test actual field installations, will have equipment, such as cable racks, already in place and supported by it.

There are a number of advantages of this embodiment of my invention which simplify its use in the field. When it is desired to be used, the load on the rod from the anchor is first temporarily removed by providing a temporary support, such as by placing stanchions under the load or scaffolding or whatever in the specific situation will most easily support the existing load apart from the anchor to be tested. Depending on whether there are any obstructions or other equipments, it may be necessary to use leveling pins or jack screws of greater length to avoid these intervening obstructions. In the following description it is to be appreciated that in many instances the operator or craftsperson will be working with his or her hands extending above his or her head; my device provides that at each stage as little weight needs to be supported as possible.

Accordingly, the split extension bar 45 is first attached to the rod 40 from the anchor to be tested and the jack screw 46 initially tensioned. The plate 30 with its leveling pads or jack screws 31 is then positioned. The rod 38 extending from the plate 30 is screwed into the screw rod block, not shown, between the split parts of the extension bar by rotation of the cylindrical housing or coilar 34 which is held by the ring 35 attached to the plate 30. Next the cam assembly 10, which advantageously includes the two cam elements, is positioned on the outer end of the plunger 26, which end is screwed into the slidable coupler or sleeve 36 within the cylindrical extension or housing 34. In this way, the full weight of the device need not be manually supported during such installation.

In the above embodiments I have employed aluminum as the basic material to minimize the total weight of the device to of the order of 20 pounds or less, depending on the size of the spring assembly and the length of the jack screws employed. While aluminum has sufficient strength and hardness to withstand the pressures and forces applied during testing operations using my device, I have employed hardened steel for the bearing surfaces and spring steel for the spring 7. Further, while in these embodiments a compression spring has been employed, other springs such as tensile springs or stacked spring washers could also be utilized.

In the use of devices in accordance with my invention, the leveling pads or jack screws determine an initial load. The cam or other separating means then serves to transfer the force of the calibrated spring to the device under test. When the extension bar is utilized, the initial pre-load due to the level pads or jack screws can be varied. Thus, considering the extension bar just as a leverage bridge adapter, different length bars or different placements of the bar leveling pad will result in different leverage factors. Depending on the leverage factor utilized, the gauge reading will require different multiplying factors to determine the test load for a given measured spring displacement.

While my device is intended to apply a load to anchorages on a static basis and in a short time, the load could be left in position for an extended period, such as 24 hours, to detect any creep in the anchorage being tested. Further, while I have described removing the present load from the hardware, my device may also be employed in situations where the existing load is left in place and an incremental load or force applied with my device.

CONCLUSION

Thus, my invention enables the user to apply a designated loading to anchorage hardware on a surface, such as a ceiling, or to an attachment to a surface or a protrusion from the surface (referred to collectively as "anchorage hardware"). This loading may be used to determine the ability of the anchorage hardware to sustain loads. The testing may be accomplished in a minimal amount of space, with minimal or no disruption to other anchorage hardware or equipment in proximity to the anchorage hardware under test, and in any position or orientation.

Numerous alternative embodiments of the invention may be devised by those skilled in the art without departure from the spirit and scope of the following claims.

We claim:
1. A device for applying a force to hardware on a surface and comprising
   a mounting frame,
   an enclosure secured to said mounting frame away from the surface and including a coupler member slidably positioned therein,
   means extending through said frame, secured to said coupler member and attachable to the hardware,
   a housing member spaced from said enclosure
   spring means within said housing member and means connecting said spring means to said coupler member, and
   means for increasing the spacing between said encloser and said housing member to cause said spring means to generate a force to apply through said connecting means and said coupler member to the hardware to be tested.

2. A device in accordance with claim 1 wherein said means connecting said spring means to said coupler member comprises a rod extending from said housing member and into said coupler member.

3. A device in accordance with claim 1 wherein said means for increasing the spacing comprises a rotatable cam positioned between said enclosure and said housing member.

4. A device in accordance with claim 3 further comprising a bearing surface on the surface of said housing member adjacent to said cam and a bearing surface on the surface of said enclosure, adjacent to said cam, said cam bearing against both said bearing surfaces.

5. A device in accordance with claim 4 further comprising lever means for rotating said cam.

6. A device in accordance with claim 1 further comprising gauge means supported by said housing member for measuring displacement of said spring means.

7. A device in accordance with claim 1 wherein said enclosure has an aperture through one side thereof for visual inspection of the displacement of said coupler member.

8. A device in accordance with claim 1 wherein said enclosure is cylindrical and secured to said mounting frame to allow rotation thereof.

9. A device in accordance with claim 1 wherein said means attachable to said anchorage hardware includes an extension bar assembly whereby said device may be offset from the hardware.

10. A device in accordance with claim 9 further comprising a first bearing surface on the upper surface of said spring assembly and a second bearing surface on the lower surface of said enclosure, said cam bearing against both of said bearing surfaces.

11. A device for applying a test force to anchorage hardware and comprising:
   a plate having a hole therethrough, a plurality of jack screws on one surface thereof, and an enclosure on the opposing surface thereof and communication with said hole,
   a slidable coupler within said enclosure,
   a rod slidably extending through said hole and connected to said coupler, one end of said rod being attachable to the anchorage housing,
   a spring assembly spaced from said enclosure and including a spring and means connecting said spring to said coupler, and
   means positioned between said enclosure and said spring assembly for determining the spacing between said plate and said spring assembly to generate a force to apply through said rod to the anchorage hardware to be tested.

12. A device in accordance with claim 11 wherein said spacing determining means comprises a rotatable cam positioned between said enclosure and said spring assembly.

13. A device in accordance with claim 12 further comprising a first bearing surface on one surface of said spring assembly and a second bearing surface on one surface of said enclosure, said cam bearing against both of said bearing surfaces.

14. A device in accordance with claim 11 wherein said spring assembly includes a gauge for indicating displacement of said spring.

15. A device in accordance with claim 11 wherein said enclosure is a cylinder and is rotatably supported by said plate.

16. A device in accordance with claim 11 and further comprising a split extension bar assembly connected to said rod for off-set attachment to the anchorage assembly.

17. A device for applying a test force to an anchorage hardware on a surface and comprising mounting means supporting an enclosure within which is positioned a slidable coupler, means for attaching said coupler to the anchorage hardware and means for supporting said mounting means from the surface, spring means, and means for transferring the force of said spring means to the anchorage hardware under test through said slidable coupler.

18. A device for applying a test force to an anchorage hardware on a surface and comprising mounting means supporting an enclosure within which is positioned a slidable coupler, means for attaching said coupler to the anchorage hardware and means for supporting said mounting means from the surface, spring means, and means for transferring the force of said spring means to the anchorage hardware under test through said slidable coupler.

19. A device in accordance with claim 18 wherein said means for increasing said spacing includes a rotatable cam bearing on surfaces of said spring housing and said enclosure.

20. A device for applying a test force to anchorage hardware on a surface and comprising a mounting frame and means for positioning said frame from said surface, an enclosure secured to said mounting frame away from the surface and including a coupler member slidably positioned therein, means connected to said coupler member and attachable to the anchorage hardware, a housing member spaced from said enclosure, spring means within said housing member and means connecting said spring means to said coupler member, and means for increasing the spacing between said enclosure and said housing member to cause said spring means to generate a force to apply through said connecting means and said coupler member to the anchorage hardware to be tested.

* * * * *